(12) United States Patent
Siebel

(10) Patent No.: US 9,861,489 B2
(45) Date of Patent: Jan. 9, 2018

(54) KNEE PROSTHESIS

(76) Inventor: Thomas Siebel, Saarbrücken (DE)

( * ) Notice: Subject to any disclaimer, the term of this patent is extended or adjusted under 35 U.S.C. 154(b) by 796 days.

(21) Appl. No.: 12/310,695

(22) PCT Filed: Sep. 7, 2007

(86) PCT No.: PCT/DE2007/001623
§ 371 (c)(1),
(2), (4) Date: Mar. 4, 2009

(87) PCT Pub. No.: WO2008/028481
PCT Pub. Date: Mar. 13, 2008

(65) Prior Publication Data
US 2010/0016976 A1    Jan. 21, 2010

(30) Foreign Application Priority Data
Sep. 8, 2006 (DE) .......................... 10 2006 042 829

(51) Int. Cl.
*A61F 2/38* (2006.01)

(52) U.S. Cl.
CPC ............ *A61F 2/389* (2013.01); *A61F 2/3859* (2013.01)

(58) Field of Classification Search
CPC ...... A61F 2/3872; A61F 2/3868; A61F 2/389; A61F 2002/3895
USPC ................... 623/20.3, 20.34, 20.35
See application file for complete search history.

(56) References Cited

U.S. PATENT DOCUMENTS

| | | | |
|---|---|---|---|
| 5,824,104 A * | 10/1998 | Tuke | A61F 2/3868 623/20.32 |
| 6,013,103 A | 1/2000 | Kaufman et al. | |
| 6,402,786 B1 * | 6/2002 | Insall et al. | 623/20.35 |
| 7,326,252 B2 * | 2/2008 | Otto | A61F 2/3836 623/20.15 |
| 2004/0006393 A1 * | 1/2004 | Burkinshaw | 623/20.3 |
| 2004/0102852 A1 * | 5/2004 | Johnson | A61F 2/38 623/20.15 |
| 2004/0243244 A1 * | 12/2004 | Otto | A61F 2/3836 623/20.27 |
| 2006/0116772 A1 * | 6/2006 | Haidukewych | 623/20.34 |
| 2008/0161918 A1 * | 7/2008 | Fankhauser | A61F 2/38 623/14.12 |

FOREIGN PATENT DOCUMENTS

| | | |
|---|---|---|
| DE | 202004003133 | 7/2004 |
| EP | 1 518 521 | 3/2005 |
| WO | 94/09725 | 5/1994 |
| WO | 2006092167 | 9/2006 |

\* cited by examiner

*Primary Examiner* — Bruce E Snow
*Assistant Examiner* — Melissa Hoban
(74) *Attorney, Agent, or Firm* — Lucas & Mercanti, LLP; Klaus P. Stoffel

(57) ABSTRACT

The invention relates to a knee prosthesis with a tibial part (1) that has concave or plane condylar bearing surfaces (2, 3). According to the invention, the lateral condylar bearing surface (2) merges into a preferably convex end portion (4) that falls away in the dorsal direction.

9 Claims, 5 Drawing Sheets

(a)

(b)

(c)

(a)

(b)

(c)

(d)

KNEE PROSTHESIS

BACKGROUND OF THE INVENTION

The invention concerns a knee prosthesis with a tibial implant that has concave or planar condylar bearing surfaces.

Tibial implants of this type are well known by use. They are sometimes used in conjunction with femoral implants, which have a medial condylar component and a lateral condylar component corresponding to the bearing surfaces of the tibial implant.

SUMMARY OF THE INVENTION

The objective of the invention is to create a new knee prosthesis of the aforementioned type that is improved in its functional capabilities, especially with respect to flexions of the knee.

The knee prosthesis of the invention which solves this problem is characterized by the fact that the lateral condylar bearing surface has an end section that slopes away in the dorsal direction.

The advantage of this is that the downwardly sloping end section of the lateral condylar bearing surface allows trouble-free luxation during knee flexion, which is associated with, among other things, a rotation of the femur about an axis perpendicular to the tibial plateau. The lateral femoral condyle or the lateral femoral component of the knee prosthesis can slide off the lateral bearing surface of the tibial implant. In conventional knee prostheses, the tibial and femoral components of the prosthesis come into contact with each other when the knee is bent, which limits the angle of flexion.

The lateral condylar bearing surface can make the transition to the downwardly sloping end section via a convexly curved transition section, and the end section itself is preferably convexly curved.

The end section extends in the dorsal direction, preferably over about one fifth to one third of the length of the lateral condylar bearing surface.

In another embodiment of the invention, the lateral condylar component of a femoral implant of the knee prosthesis has an extension, which comes into contact with the sloping end section during flexion of the knee. Advantageously, this extension forms both a lever and a guide, which facilitate the sliding of the lateral condylar component off the condylar bearing surface.

This extension preferably has a contact surface that is complementary to the end section.

In another embodiment of the invention, the medial condylar bearing surface can be shaped as a depression that widens in the dorsal direction. The advantage of this is that this depression ensures that during flexion of the knee, the contact area between the condylar bearing surface and the medial condyle does not experience an undesired shift in the ventral direction.

In another embodiment of the invention, an elevation with a third bearing surface is formed between the condylar bearing surfaces in the dorsal half of the implant. A projection formed between the condylar components of a femoral implant can be supported on this third bearing surface. Advantageously, this support assists the return rotation of the femur relative to the tibial implant during a flexion of the knee by facilitating the upward movement of the femur implant up the downwardly sloping end section that is necessary during the return movement.

This third bearing surface can be partly formed by a dorsal extension on the tibial implant and preferably ascends towards the free end of the dorsal extension. Corresponding to the rotation of the femoral implant relative to the tibial implant, the third bearing surface preferably runs in a curve that follows the contour of the medial condylar bearing surface.

In another embodiment of the invention, the downwardly sloping end section of the lateral condylar bearing surface makes a transition to another bearing surface that extends perpendicularly to the tibial plateau. An advantage here is that the luxated femur does not lie against the tibia but rather against the implant.

During prolonged knee flexion, e.g., while sitting on the floor with the legs crossed or similar positions, stresses on the tibia are avoided.

The invention is explained in greater detail below with reference to the specific embodiments of the invention that are illustrated in the accompanying drawings.

DETAILED DESCRIPTION OF THE INVENTION

A tibial implant 1 of a knee prosthesis has a lateral condylar bearing surface 2 and a medial condylar bearing surface 3. The bearing surfaces are basically concave.

Figure 3:
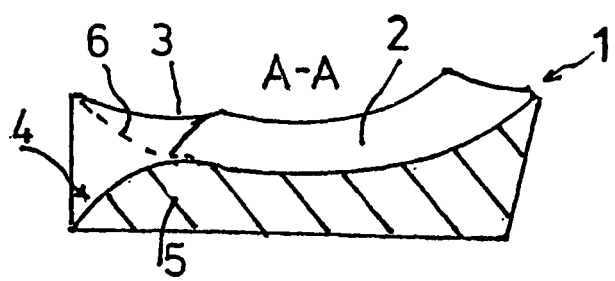
FIG. 3 shows the tibial implant of FIG. 1 along sectional line A-A.

As FIG. 3 shows, the lateral condylar bearing surface 2 comprises an end section 4, which, in a top view of the tibial plateau, slopes down to the dorsal edge of the implant. In the embodiment under consideration here, the end section 4 is convexly curved. A transition section 5 between the concave part of the condylar bearing surface 2 and the end section 4 also has concave curvature. A broken line 6 indicates the normal course of the condylar bearing surface 2 without the downwardly sloping end section 4.

During bending of the knee, in which the femur carries out a rotation relative to an axis perpendicular to the tibial plateau, the downwardly sloping end section 4 aids luxation and prevents the femur or femoral implant from striking the dorsal edge of the tibial implant 1.

Figure 4:
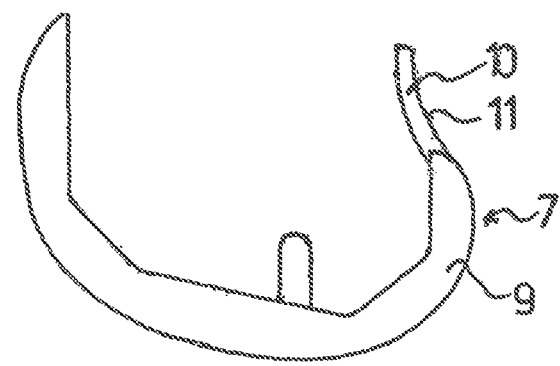
FIG. 4 is a side view of a femoral implant that can be used together with the tibial implant of FIGS. 1 to 3.
Figure 5:
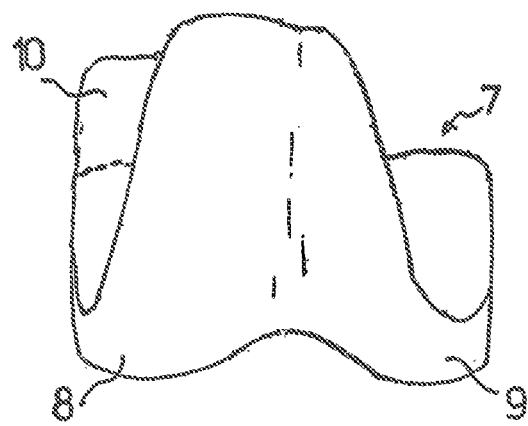
FIG. 5 shows the femoral implant of FIG. 4 as viewed in the dorsal direction.

A femoral implant 7 shown in FIG. 4 can be advantageously used together with the tibial implant 1 described with reference to FIGS. 1 to 3.

The femoral implant 7 has a lateral condylar component 8 and a medial condylar component 9. An extension 10 with a contact surface 11 is connected to the dorsal end of the lateral condylar component 8. The contact surface 11 is designed to be approximately complementary to the end section 4 of the condylar bearing surface 2 of the tibial implant 1.

During a flexion of the knee, the contact surface 11 of the extension 10 contacts the end section 4. On the one hand, this produces leverage, and, on the other hand, the femoral implant 7 is exactly supported on the tibial implant 1 by the extension resting against it. Both facilitate luxation, i.e., the sliding of the condylar component 8 off the condylar bearing surface 2.

In the embodiments described below, parts that are the same or have the same function are designated by the same reference number as in the preceding drawings except that the letter a, b, c, d, e, or f is added to the given reference number.

Figure 1:
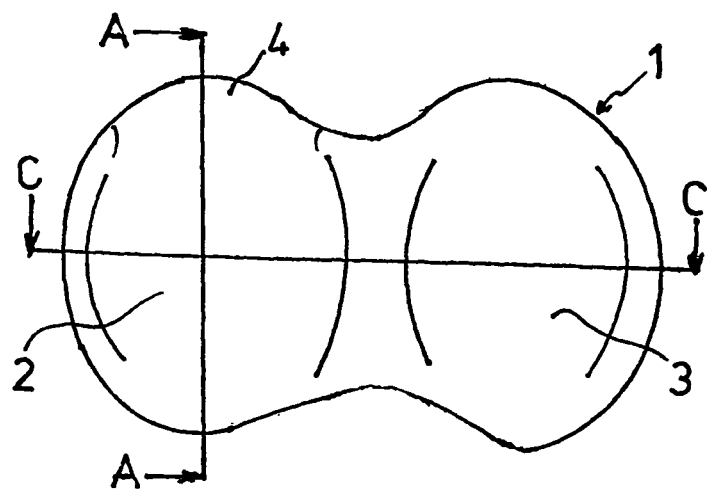
FIG. 1 is a top view of the plateau of a tibial implant of the invention.
Figure 2:
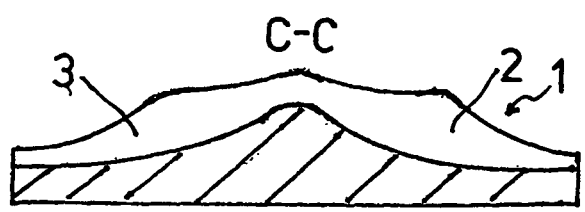
FIG. 2 shows the tibial implant of FIG. 1 along sectional line C-C.
Figure 6:
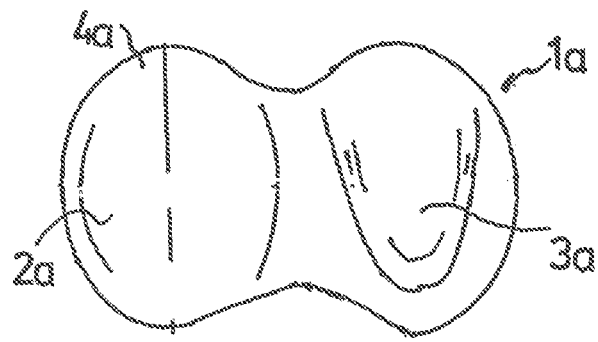
FIGS. 6 and 7 show additional embodiments of a tibial implant of the invention in top views of the implant.

The tibial plateau of FIG. 6 differs from the tibial plateau of FIG. 1 in that a medial condylar bearing surface 3a is formed as a depression, whose width increases in the dorsal direction as indicated by the contour line 12. This shaping of the overall concave condylar bearing surface 3a ensures that the contact area of the medial condyle of the femur or of the medial condylar component of a femoral implant during flexion, in which the femur rotates about an axis perpendicular to the tibial plateau, does not shift in the ventral direction but rather, as viewed in the ventral direction, remains approximately in the first third of the medial condylar bearing surface 3a.

Figure 7:
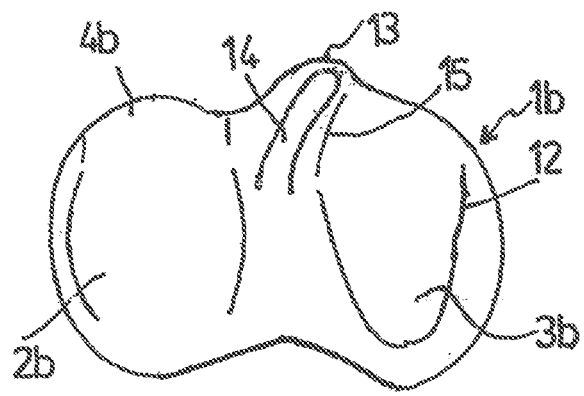

Besides a condylar bearing surface 3b, which corresponds to the condylar bearing surface 3a, the tibial implant 1b shown in FIG. 7 additionally has a dorsal extension 13. The extension 13 forms part of a third condylar bearing surface 14 that extends between the condylar bearing surfaces 2b and 3b. This third bearing surface 14 ascends in the dorsal direction to the free end of the extension 13 and runs in the form of an arc that follows approximately a contour 15 of the medial condylar bearing surface 3b.

Figure 8:
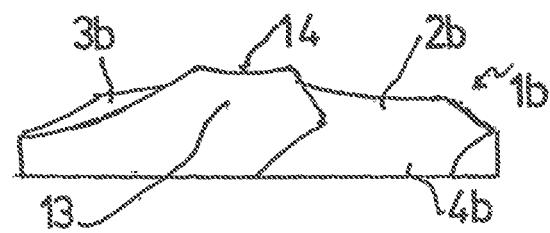
FIG. 8 shows the tibial implant of FIG. 7 as viewed in the ventral direction.
Figure 9:
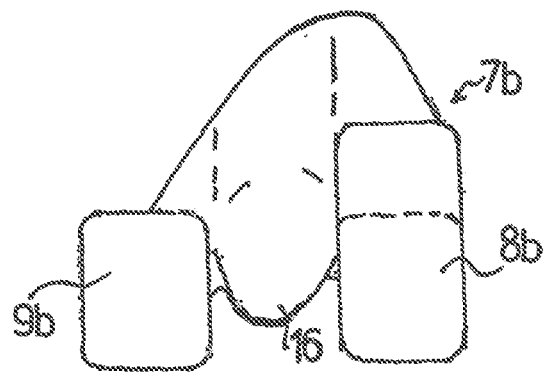
FIG. 9 shows a femoral implant that can be used with the tibial implant of FIGS. 7 and 8 in a knee prosthesis as viewed in the ventral direction.

The tibial implant shown in FIGS. 7 and 8 can be used in a knee prosthesis together with the femoral implant 7b shown in FIG. 9.

In addition to a lateral condylar component 8b and a medial condylar component 9b, the femoral implant 7b has a projection 16 between the condylar components.

If, during an extension of the flexed knee, the femur is to move back into the rotational position corresponding to the unflexed knee, the return rotation of the femur associated with this requires that the lateral condyle 8b slide up the end section 4b to the concave part of the condylar bearing surface 2b.

This necessitates lifting of the femur, which is accomplished by virtue of the fact that during the extension, the projection 16 comes into contact with the third bearing surface 14, which has a curvature in accordance with the necessary rotation of the femur.

Figure 10:
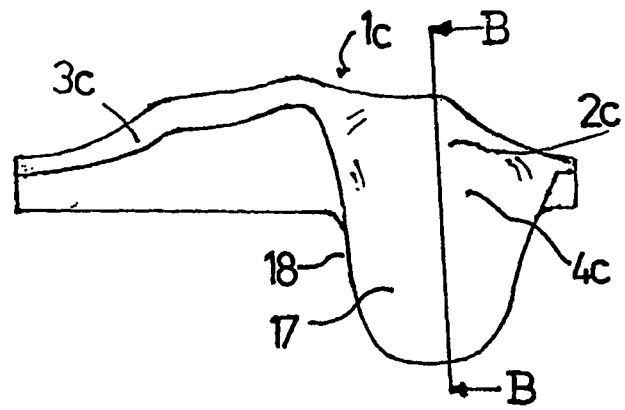
FIG. 10 is a side view of another embodiment of a tibial implant of the invention as viewed in the ventral direction.
Figure 11:
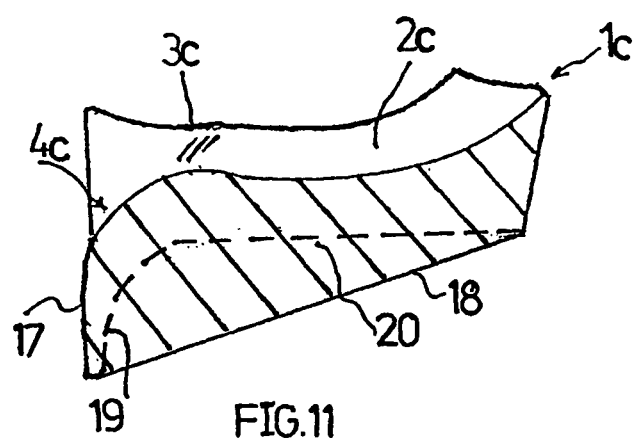
FIG. 11 shows the tibial implant of FIG. 10 along, sectional line B-B.

In the tibial implant 1c shown in FIGS. 10 and 11, a downwardly sloping section 4c of a lateral condylar bearing surface 2c makes a transition to another bearing surface 17, which extends basically perpendicularly to the tibial plateau. The other bearing surface 17 is formed by an extension 18 that projects in the direction of the tibia. In the illustrated embodiment, the projecting length of the extension 18 decreases linearly towards the ventral edge of the tibial plateau 1c. A milled-out recess for receiving an insert of this type can be produced during the implantation with comparatively little effort. Alternatively, the additional bearing surface could also be formed by a projecting tongue, as is indicated in FIG. 11 by a broken line.

During the luxation, the femur makes contact with the additional bearing surface 17. Especially during prolonged flexions, such as occur while sitting on the floor, the implant protects the tibia from long-term stress by the luxated femur.

Figure 12:
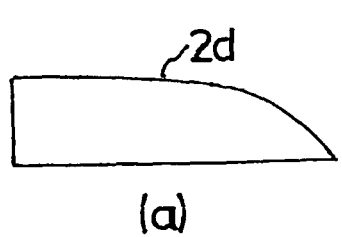
FIGS. 12 to 14 show further embodiments of tibial implants of the invention.
Figure 12:
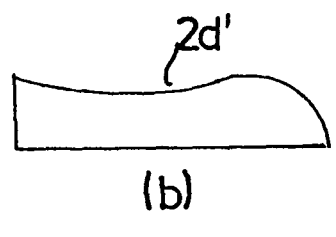
Figure 12:
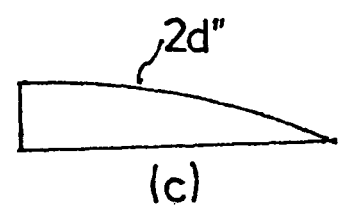

FIG. 12 shows additional forms of tibial implants with different condylar bearing surfaces 2d, 2d', and 2d". The condylar bearing surface 2d" is shaped convexly in the form of a circular arc.

Figure 13:
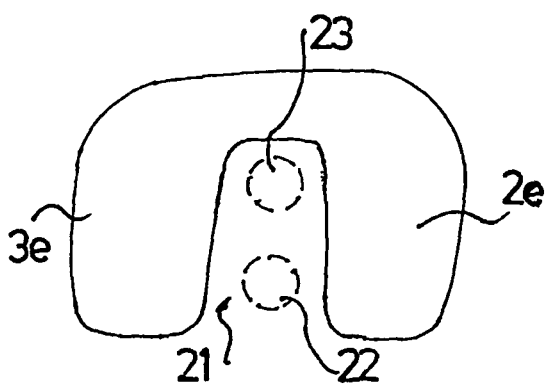

FIG. 13 shows a top view of a tibial implant with condylar bearing surfaces 2e and 3e. The implant has a recess through which cruciate ligaments 22 and 23 can pass.

Figure 14:
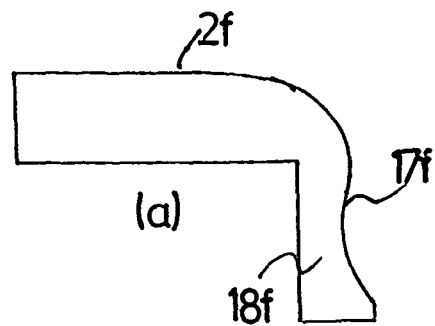
Figure 14:
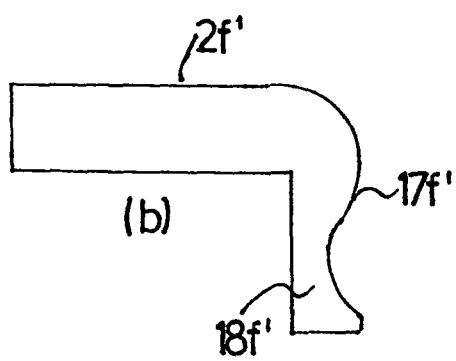
Figure 14:
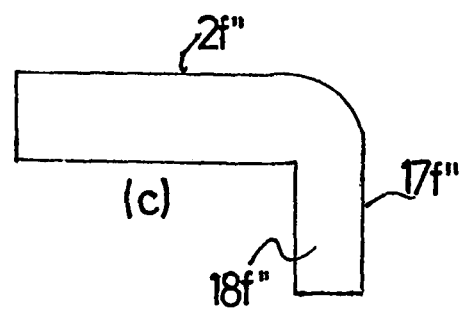
Figure 14:
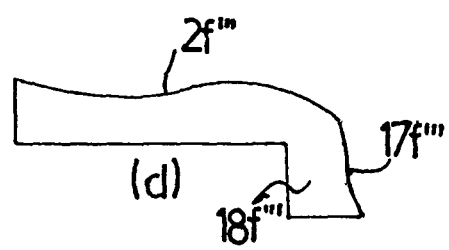

FIG. 14 shows additional tibial implants with condylar bearing surfaces 2f and extensions 18f. The extensions 18f have various additional bearing surfaces 17f, 17f", 17f", and 17f"".

The invention claimed is:

1. A knee prosthesis comprising a tibial implant (1) that has a tibial plateau with concave or planar condylar bearing surfaces (2, 3) on which a lateral condylar component of a femur or a femoral implant of the knee prosthesis slides during flexion of the knee, wherein the bearing surfaces include a lateral condylar bearing surface (2) that transitions into an end section (4) that extends to a dorsal end of the tibial implant and slopes away in a dorsal direction via a convexly curved transition section, wherein the end section (4) extends in the dorsal direction over about one fifth to one third of a length of the lateral condylar bearing surface (2) and is convexly curved, so that the lateral condylar component of the femur or the femoral implant of the knee prosthesis slides off the end section during flexion of the knee and prevents an impact of the femur or the femoral implant against the tibial implant, wherein an extension (18) forms a dorsal bearing surface (17) that extends perpendicularly to the tibial plateau, the extension (18) and the dorsal bearing surface (17) projecting from an underside of the tibial implant (1c) that faces away from the bearing surfaces (2c, 3c) and having a width substantially equal to a width of the downwardly sloping end section (4), wherein the downwardly sloping end section (4c) of the lateral condylar bearing surface (2c) forms a transition to the dorsal bearing surface (17), the downwardly sloping end section and the dorsal bearing surface having smooth directional transitions and being free of corners and edges.

2. A knee prosthesis in accordance with claim 1, wherein the lateral condylar component of the femoral implant (7) of the knee prosthesis has an extension (10), which comes into contact with the end section (4) during flexion of the knee.

3. A knee prosthesis in accordance with claim 2, wherein the extension (10) has a contact surface (11) that is complementary to the end section (4).

4. A knee prosthesis in accordance with claim 1, wherein the bearing surfaces include a medial condylar bearing surface (3a; 3b) that is formed as a depression (12) that widens in the dorsal direction.

5. A knee prosthesis in accordance with claim 1, wherein an elevated third bearing surface (14) is formed between the condylar bearing surfaces (2b, 3b) in a dorsal half of the tibial implant and that a projection (16) formed between the condylar components (8b, 9b) of the femoral implant (7b) can be supported on this third bearing surface (14).

6. A knee prosthesis in accordance with claim 5, wherein the tibial implant as a dorsal extension (13) and the third bearing surface (14) is partly formed by the dorsal extension (13) of the tibial implant (1*b*).

7. A knee prosthesis in accordance with claim 6, wherein the third bearing surface (14) ascends towards a free end of the dorsal extension (13).

8. A knee prosthesis in accordance with claim 6, wherein the third bearing surface (14) runs in a curve that substantially follows a contour (15) of a medial condylar bearing surface (3*b*).

9. A knee prosthesis in accordance with claim 1, wherein a projecting length of the extension (18) decreases towards a ventral side of the tibial plateau (1*c*).

* * * * *